(12) United States Patent
Williams et al.

(10) Patent No.: US 11,389,151 B2
(45) Date of Patent: Jul. 19, 2022

(54) MODULAR RETRACTOR SYSTEM

(71) Applicant: Institute for Musculoskeletal Science and Education, Ltd., King of Prussia, PA (US)

(72) Inventors: John Williams, Fort Wayne, IN (US); Seth Anderson, Mount Gretna, PA (US); Megan Stauffer, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 0 days.

(21) Appl. No.: 17/108,882

(22) Filed: Dec. 1, 2020

(65) Prior Publication Data

US 2021/0315563 A1 Oct. 14, 2021

Related U.S. Application Data

(60) Provisional application No. 62/939,143, filed on Nov. 22, 2019.

(51) Int. Cl.
*A61B 17/02* (2006.01)
*A61F 2/46* (2006.01)
(Continued)

(52) U.S. Cl.
CPC ........ *A61B 17/025* (2013.01); *A61B 17/0206* (2013.01); *A61B 90/35* (2016.02);
(Continued)

(58) Field of Classification Search
CPC ..... A61B 17/02; A61B 17/0206; A61B 17/32; A61F 2/4611
See application file for complete search history.

(56) References Cited

U.S. PATENT DOCUMENTS 5,303,694 A 4/1994 Mikhail
5,902,233 A * 5/1999 Farley ................ A61B 17/0206
600/213
(Continued)

FOREIGN PATENT DOCUMENTS

CN 202654170 U 1/2013

OTHER PUBLICATIONS

International Search Report and Written Opinion dated Aug. 13, 2021 in PCT Application No. PCT/US2021/14677.
(Continued)

*Primary Examiner* — Eduardo C Robert
*Assistant Examiner* — Steven J Cotroneo
(74) *Attorney, Agent, or Firm* — Plumsea Law Group, LLC (57) ABSTRACT

A system and method of positioning a spinal implant into an intervertebral space comprises the steps of: cutting an incision through the skin toward an intervertebral space between a L5 and S1 vertebra; inserting an uncoupled first, second and third retractor blade into the incision to pre-position the retractor blades prior to retraction; coupling the pre-positioned first retractor blade to a connector arm to connect the first retractor blade to a table arm; attaching a blade to blade connector and mini flex arm to couple the second blade to either the first blade or third blade; and wherein the three uncoupled blades, once pre-positioned and then coupled, the blades are retracted to open the incision and expose the vertebral bodies.

11 Claims, 14 Drawing Sheets

(51) Int. Cl.
*A61B 90/35* (2016.01)
*A61B 17/00* (2006.01)
*A61B 17/56* (2006.01)

(52) U.S. Cl.
CPC ... *A61F 2/4611* (2013.01); *A61B 2017/00473* (2013.01); *A61B 2017/0256* (2013.01); *A61B 2017/564* (2013.01); *A61B 2560/0443* (2013.01)

(56) References Cited

U.S. PATENT DOCUMENTS

| | | | |
|---|---|---|---|
| 5,928,139 A * | 7/1999 | Koros | A61B 17/0206 600/205 |
| 5,931,777 A | 8/1999 | Sava | |
| 5,944,658 A | 8/1999 | Koros et al. | |
| 5,984,865 A | 11/1999 | Farley et al. | |
| 7,556,600 B2 | 7/2009 | Landry et al. | |
| 7,785,253 B1 * | 8/2010 | Arambula | A61B 1/32 600/219 |
| 7,850,608 B2 | 12/2010 | Hamada | |
| 7,931,589 B2 | 4/2011 | Cohen et al. | |
| 7,946,982 B2 | 5/2011 | Hamada | |
| 7,981,029 B2 | 7/2011 | Branch et al. | |
| 8,114,016 B2 * | 2/2012 | Lo | A61B 17/0206 600/202 |
| 8,303,499 B2 | 11/2012 | Hamada | |
| 8,353,826 B2 | 1/2013 | Weiman | |
| 8,636,657 B2 | 1/2014 | Hamada | |
| 8,876,904 B2 | 11/2014 | Pimenta et al. | |
| 8,968,363 B2 | 3/2015 | Weiman et al. | |
| 9,095,301 B2 | 8/2015 | Hamada | |
| 9,451,940 B2 | 9/2016 | Spann | |
| 9,486,199 B2 | 11/2016 | Pimenta et al. | |
| 9,622,732 B2 | 4/2017 | Martinelli et al. | |
| 9,848,862 B2 | 12/2017 | Bass et al. | |
| 10,085,854 B2 | 10/2018 | Spann | |
| 10,130,348 B2 | 11/2018 | Cryder et al. | |
| 10,238,375 B2 * | 3/2019 | O'Connell | A61B 17/0293 |
| 10,278,786 B2 * | 5/2019 | Friedrich | A61B 17/0206 |
| 10,687,830 B2 | 6/2020 | Garcia-Bengochea et al. | |
| 10,959,860 B2 | 3/2021 | Spann | |
| 2001/0037123 A1 * | 11/2001 | Hancock | A61B 17/0206 606/167 |
| 2001/0041828 A1 * | 11/2001 | Deckman | A61B 17/0206 600/232 |
| 2002/0099269 A1 | 7/2002 | Martin et al. | |
| 2005/0159651 A1 | 7/2005 | Raymond et al. | |
| 2008/0140085 A1 * | 6/2008 | Gately | A61F 2/4465 606/99 |
| 2011/0130793 A1 * | 6/2011 | Woolley | A61B 17/7076 606/279 |
| 2012/0010472 A1 * | 1/2012 | Spann | A61F 2/447 600/214 |
| 2012/0271118 A1 * | 10/2012 | White | A61B 17/02 600/226 |
| 2013/0023735 A1 | 1/2013 | Brown et al. | |
| 2013/0204262 A1 | 8/2013 | Menendez | |
| 2013/0345520 A1 | 12/2013 | Hamada | |
| 2014/0257039 A1 * | 9/2014 | Feldman | A61B 17/02 600/205 |
| 2014/0350347 A1 * | 11/2014 | Karpowicz | A61B 17/0206 600/215 |
| 2015/0018628 A1 * | 1/2015 | Friedrich | A61B 17/025 600/214 |
| 2015/0305731 A1 | 10/2015 | Friedrich et al. | |
| 2016/0081818 A1 * | 3/2016 | Waugh | A61B 17/0206 623/17.16 |
| 2016/0354073 A1 | 12/2016 | Nel et al. | |
| 2017/0014117 A1 * | 1/2017 | Capote | A61B 17/0206 |
| 2017/0296160 A1 | 10/2017 | O'Brien | |
| 2017/0333023 A1 * | 11/2017 | Adams | A61B 17/0293 |
| 2018/0042595 A1 * | 2/2018 | Tsubouchi | A61B 17/0206 |
| 2019/0029497 A1 | 1/2019 | Mirza et al. | |
| 2019/0105179 A1 | 4/2019 | Spann | |
| 2020/0015799 A1 | 1/2020 | Tsubouchi | |

OTHER PUBLICATIONS

Office Action dated Nov. 5, 2021 in U.S. Appl. No. 17/155,848.
Office Action dated Feb. 1, 2022 in U.S. Appl. No. 17/155,903.

* cited by examiner

MODULAR RETRACTOR SYSTEM

CROSS-REFERENCE TO RELATED APPLICATIONS

This application claims priority to U.S. Provisional Patent Application No. 62/939,143, filed Nov. 22, 2019.

FIELD OF THE INVENTION

The present disclosure relates to methods and devices for retracting tissue in a surgical procedure to allow access to the surgical site. The purpose of this Retractor System is to provide soft tissue retraction, allowing surgical access to the spine. More specifically, this invention is intended for use during Oblique (Anterior to Psoas) Lumbar Interbody Fusion Surgery at L5-S1 between the bifurcation. However, it also could be used in any surgical approach requiring soft tissue retraction.

BACKGROUND OF THE INVENTION

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray. One typical retractor system may include a plurality of blades coupled to a retractor frame. In use, the blades may be inserted into an incision and then retracted to displace tissue surrounding the incision exposing the surgical site. To minimize trauma to the tissue, this tissue displacement should be refined and controlled. However, current retractor systems do not provide desired control of the distraction. More particularly, the devices currently in use are mechanically coupled so the surgeon has limited ability to feel the resistance at the blades or to rotate the blades affixed to the retractor arm independently. This limited control takes away the skilled surgeon's ability to finely adjust the movement of the retractor blades.

The disadvantage of these systems is that the frame is positioned first and then the retractor blades are placed. The position of the retractor blades is therefore limited by the position of the frame.

In the case of 2, 3, and 4 blade ring retractors, the retraction on soft tissue is done through rigid mechanisms that do not provide tactile feel. This increases the risk of damage to vessels and other soft tissue.

Thus, there is a need for improved methods and devices that can be used for retracting tissue to provide access to the surgical site.

SUMMARY OF THE INVENTION

A system and method of positioning a spinal implant into an intervertebral space comprises the steps of: cutting an incision through the skin toward an intervertebral space between a L5 and S1 vertebra; inserting an uncoupled first, second and third retractor blade into the incision to pre-position the retractor blades prior to retraction; coupling the pre-positioned first retractor blade to a connector arm to connect the first retractor blade to a table arm; attaching a blade to blade connector and mini flex arm to couple the second blade to either the first blade or third blade; and wherein the three uncoupled blades, once pre-positioned and then coupled, the blades are retracted to open the incision and expose the vertebral bodies.

One or more of the blades have threaded Steinmann pins and the method includes securing one of the blades to the vertebra. The uncoupled blades have a handle quick connect attached to pre-position the blade. The method further comprises detaching the handle quick connect once the blade is pre-positioned.

Once retraction is complete, the step of discectomy and end plate preparation is completed, and the method further has the step of implanting an implant. The implant is inserted using an inserter on an OLIF approach of about 25 degrees off a coronal plane. The implant is inserted without the use of an orthogonal maneuver. The implant when inserted using an approach 25 degrees off the coronal plane, the lordosis of the implant will be correctly aligned with the lordosis of the spine. The implant is inserted using a straight or articulating inserter. The articulating inserter allows the surgeon to adjust the angle of the inserter handle relative to the implant to adjust the trajectory of the implant prior to inserting into the disc space or after. The system is configured to build a rigid frame outside of the body after the blades have been properly positioned by hand and pinned to a vertebral body.

The surgeon has the flexibility to place the blades wherever they want without being limited by the rigid frame ensuring that the blades are placed perfectly every time based on unique anatomic structures while still providing a rigid frame. Placing the retractor blades by hand provides the surgeon with tactile feedback to help reduce the risk of vascular injury. The blade to blade fixation eliminates the need to hold one of the blades in place during the procedure. If two blade to blade connections are used, this eliminates the need for a second table arm and removes clutter from the sterile field.

DEFINITIONS

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs. It is to be understood that this invention is not limited to the particular methodology, protocols, cell lines or type of stem cell, constructs, additives, and reagents described herein. It is also to be understood that the terminology used herein is for the purpose of describing particular embodiments only, and is not intended to limit the scope of the present invention which will be limited only by the appended claims.

OLIF—or oblique lateral interbody fusion, is a less invasive approach to spinal fusion surgery in which the neurosurgeon accesses and repairs the lower (lumbar) spine from the front and side of the body (passing in a trajectory about halfway between the middle of the stomach and the side of the body). During an OLIF procedure, the surgeon uses a corridor between the psoas muscle and the peritoneum to access the spine. The psoas muscles connect the lower back to the thighs and enable movement and flexibility of the back, pelvis, legs, and hips. The peritoneum is the membrane that lines the abdominal cavity.

Psoas—The psoas is a deep-seated core muscle connecting the lumbar vertebrae to the femur. The psoas major is the biggest and strongest player in a group of muscles called the hip flexors: together they contract to pull the thigh and the torso toward each other.

BRIEF DESCRIPTION OF THE DRAWINGS

The invention will be described by way of example and with reference to the accompanying drawings in which.

DETAILED DESCRIPTION OF THE INVENTION

Figure 1:
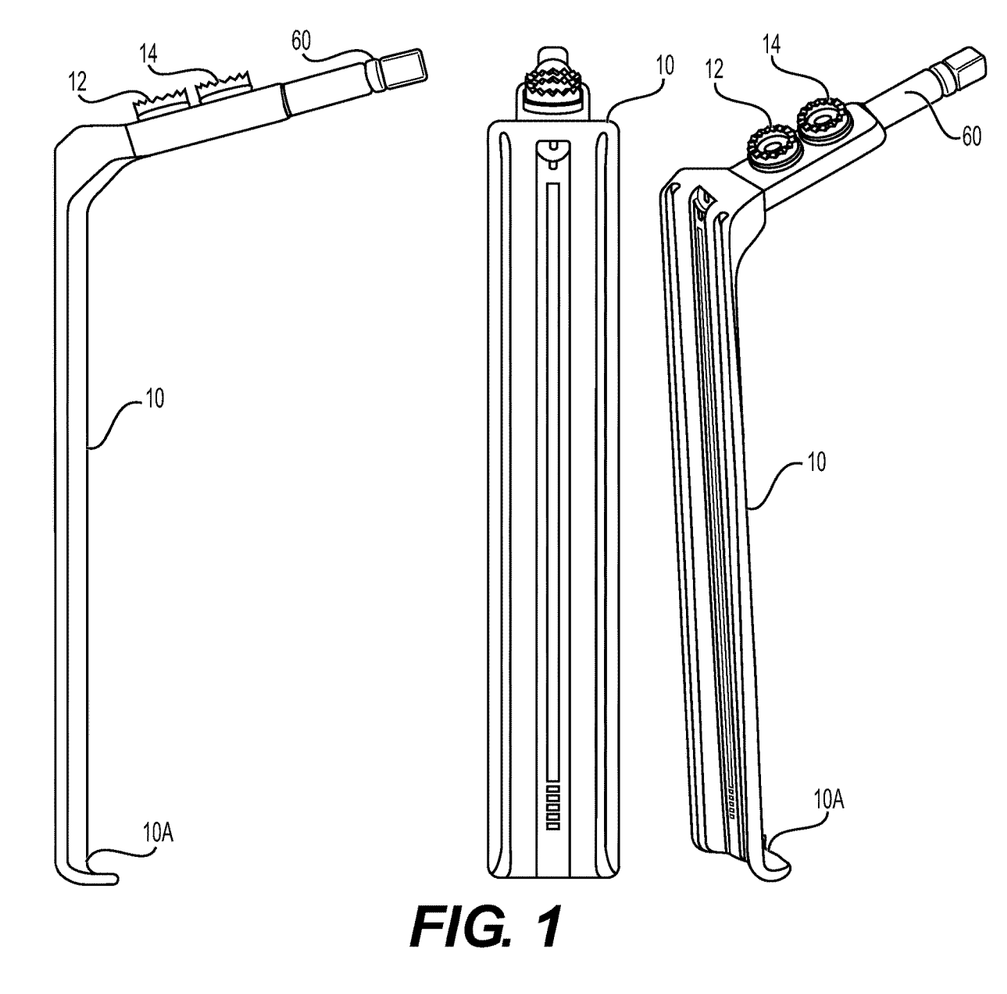
FIG. 1 is blade 1 shown in side, front and perspective views.
Figure 2A:
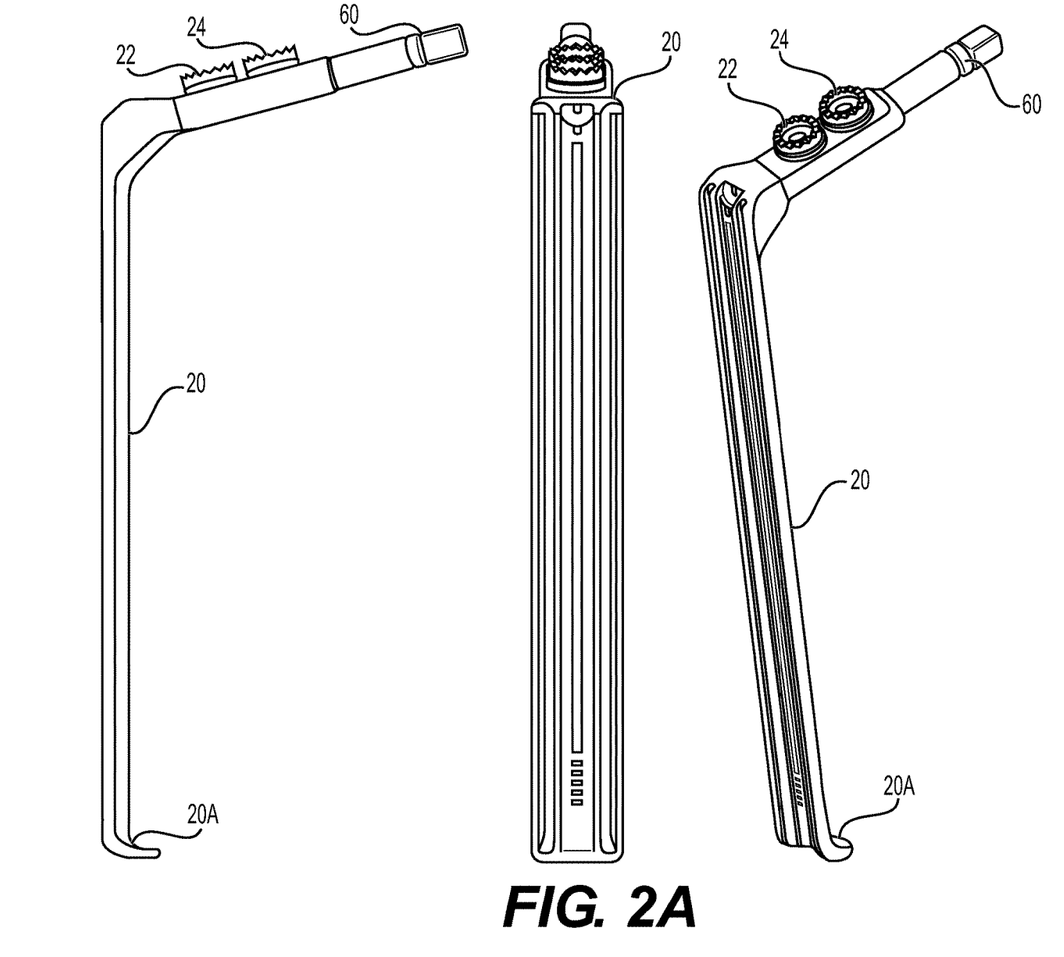
FIG. 2A is a first design option of blade 2 shown in side, front and perspective views.
Figure 2B:
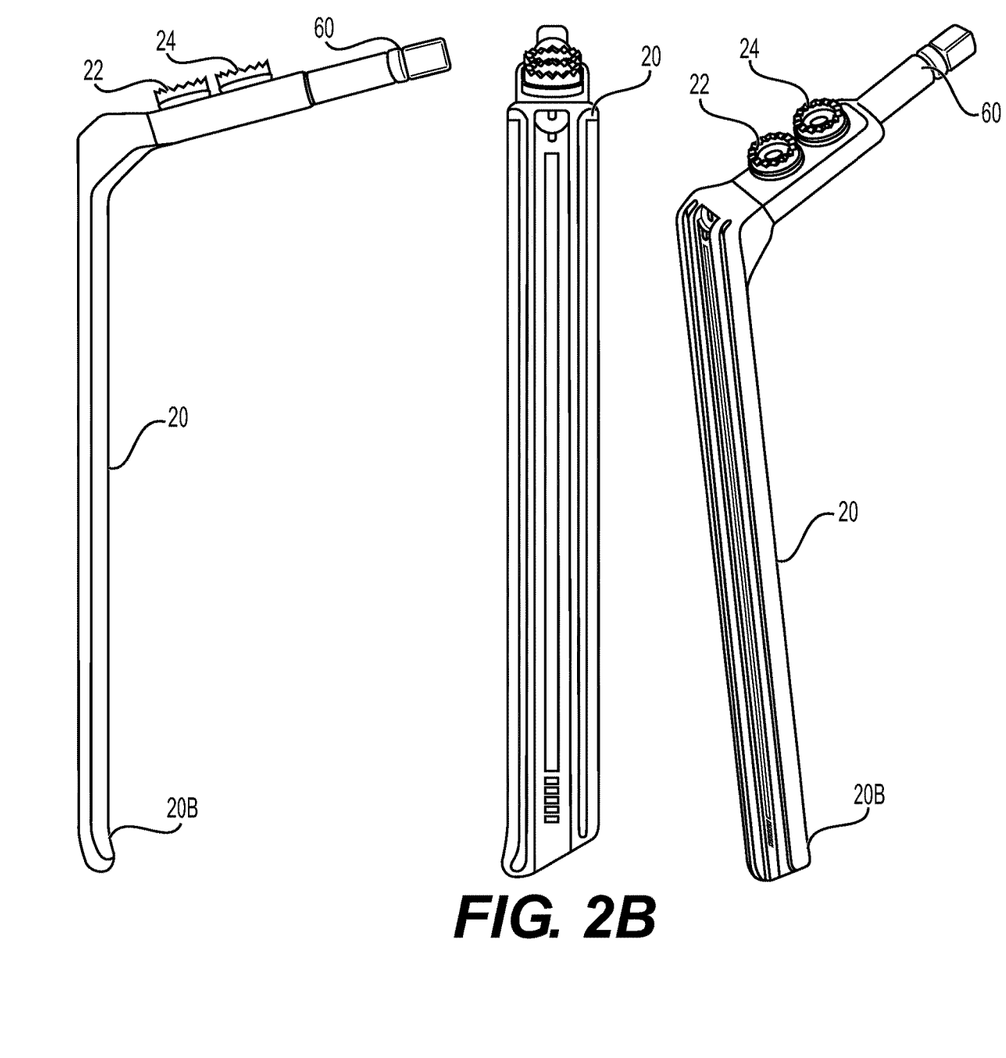
FIG. 2B is a second design option of blade 2 shown in side, front and perspective views.
Figure 3A:
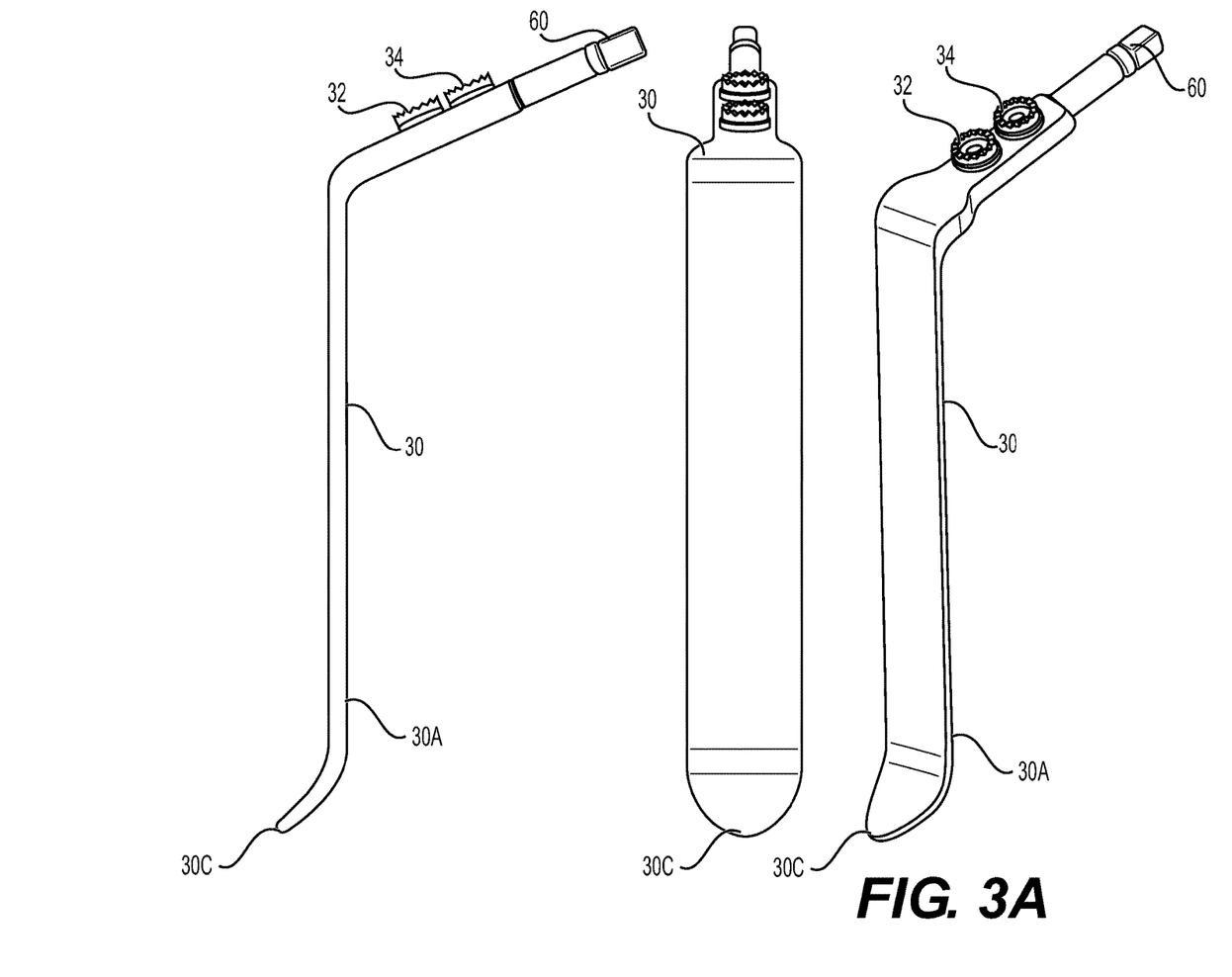
FIG. 3A is a first design option of blade 3 shown in side, front and perspective views.
Figure 3B:
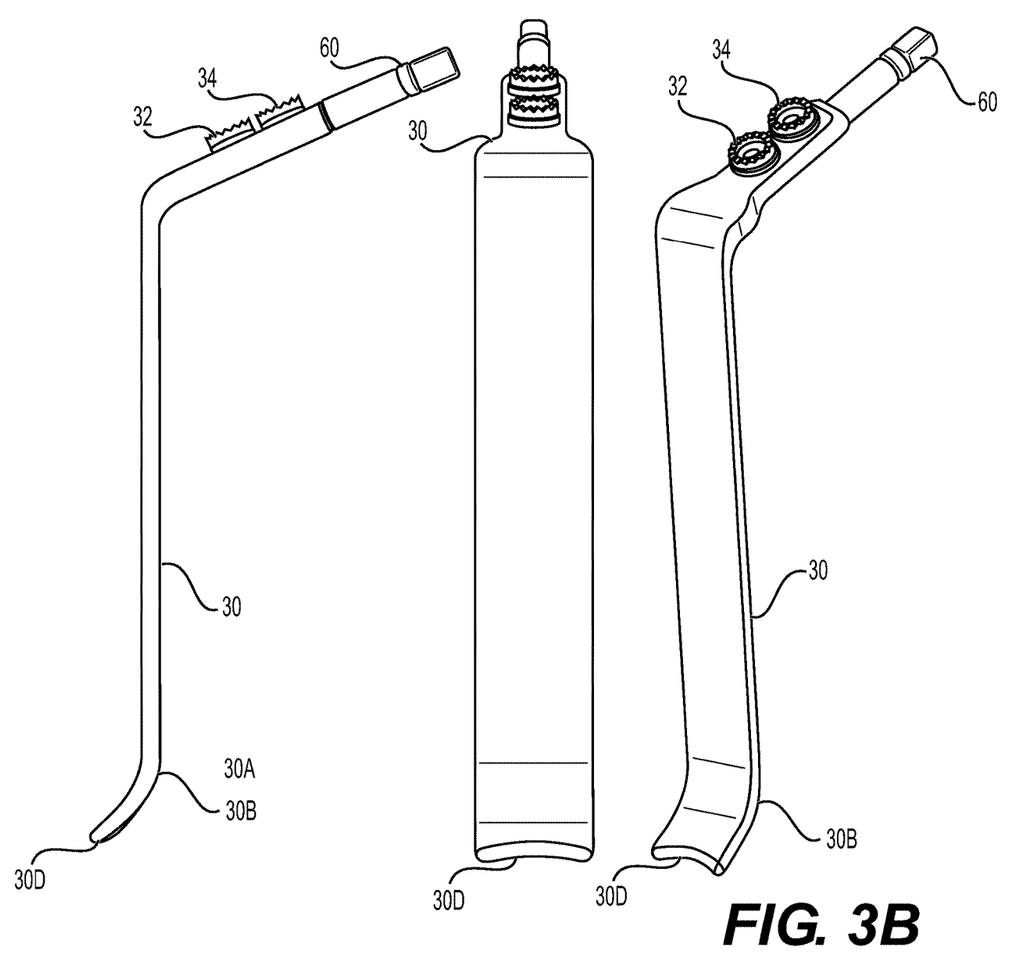
FIG. 3B is a second design option of blade 3 shown in side, front and perspective views.
Figure 4:
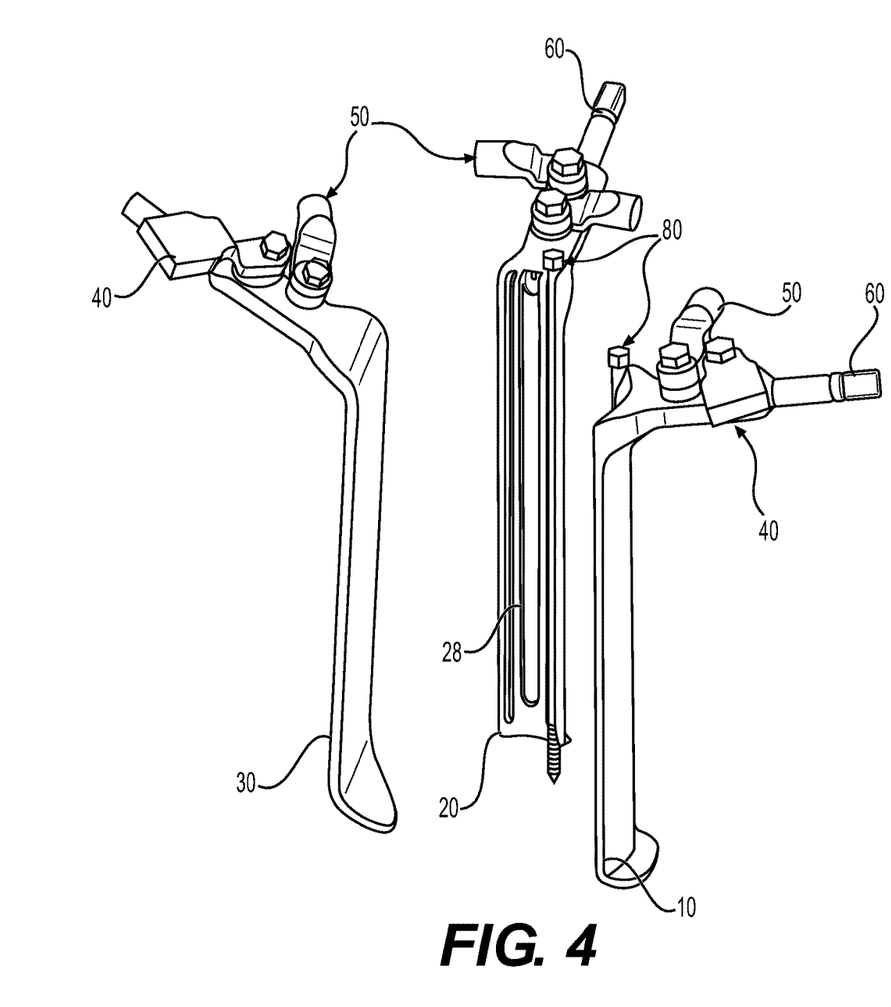
FIG. 4 is a perspective view of the combined blade system.

There are 3 retractor blades 10, 20, 30 as part of the system, designated #1 Blade 10, #2 Blade 20, and #3 Blade 30. Each Blade will come in a range of lengths (approximately 10-20 cm). Each blade 10, 20, 30 can have optional retraction ends. FIG. 1 shows blade 10 with a flanged end 10A. FIG. 2A shows blade 20 with a flanged end 20A similar to blade end 10A or as shown in FIG. 2B showing a flared out enlarged end portion of the blade 20, but without the flanged end 20A. Blade 30 can have an inclined curved end 30A with a convex tip 30C shown in FIG. 3A and in FIG. 3B, the inclined curved end 30B has a concave tip 30D. As shown in FIG. 4, variations of these blade ends can be used to retract the soft tissue.

1 Blade 10 is designed to be placed medially of the left common iliac vein, for a left sided up approach, or medially of the right common iliac vein, for a right sided up approach.

2 Blade 20 is designed to be placed caudally of the bifurcation.

3 Blade 30 is designed to be placed medially for the right common iliac vein, for a left sided up approach, or medially of the left common iliac vein for a right sided up approach. Optionally, #3 Blade 30 can include a slot for a light source, similar to slot 28 of blade 20.

A light source or shim may be placed down the T shaped channel or slot 28 of blade 20 as shown in FIG. 4.

Figure 5:
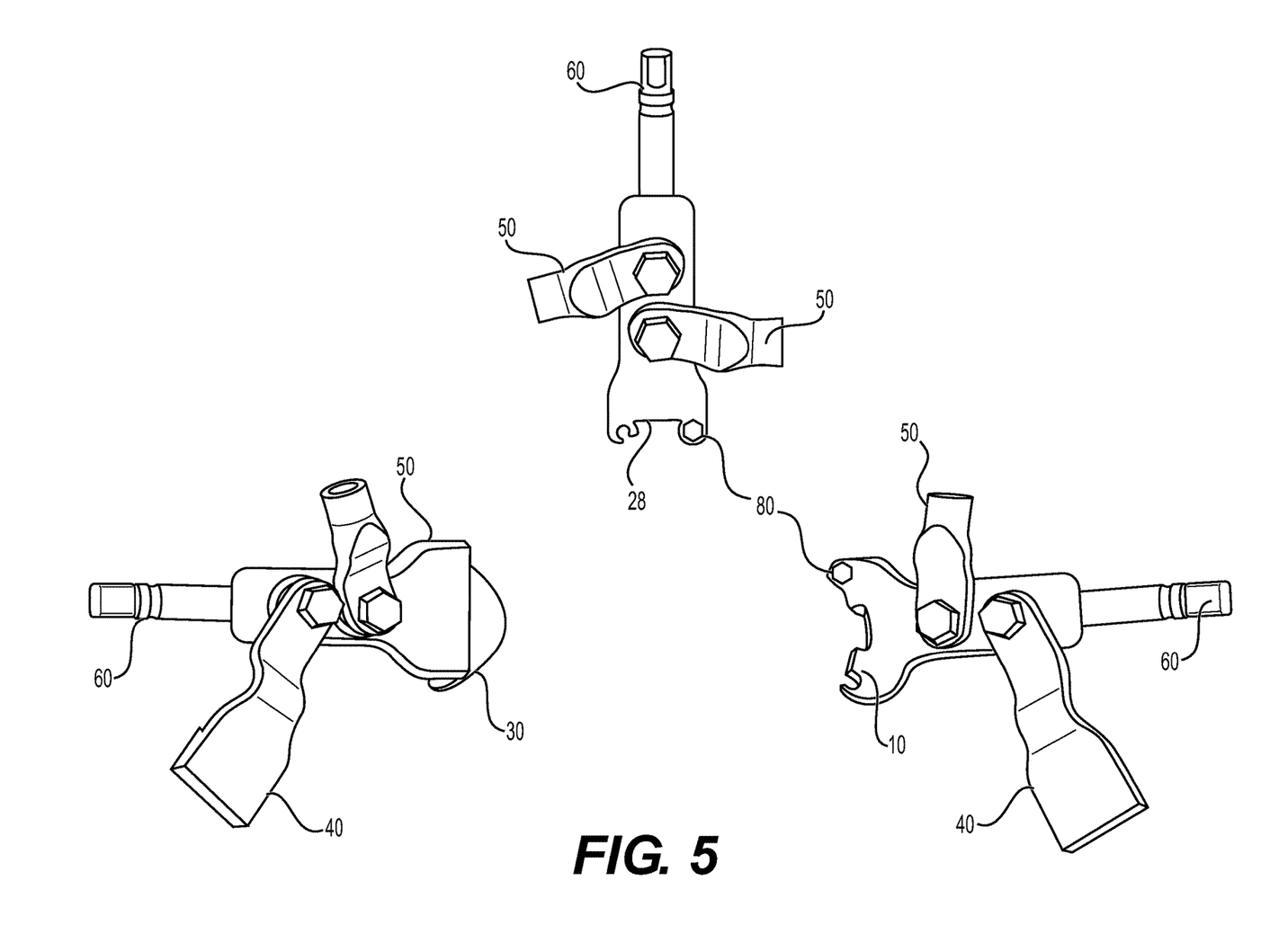
FIG. 5 shows various blade to arm connection mechanisms taken from a top view looking downwardly.

FIG. 5 shows blades with various connection mechanisms as well as threaded Steinmann Pins 80 that may be used to secure and lag the retractor blades to the vertebral bodies.

Figure 6A:
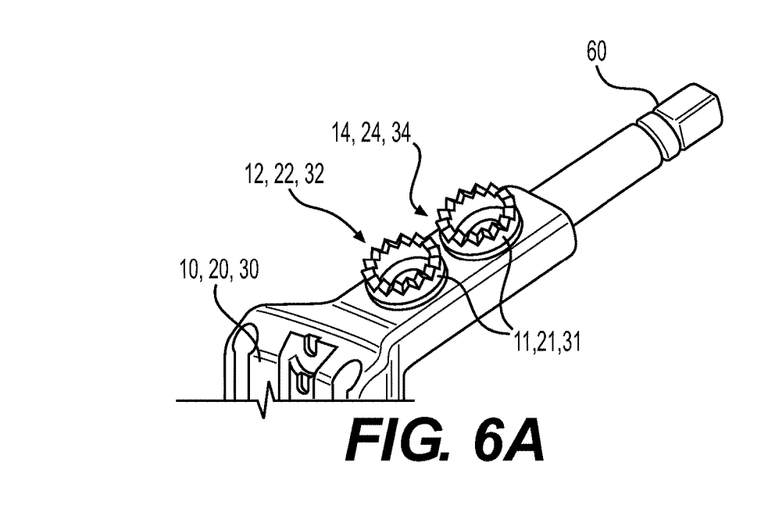
FIGS. 6A-6D show a connection mechanism being attached to a blade in sequential views.
Figure 6B:
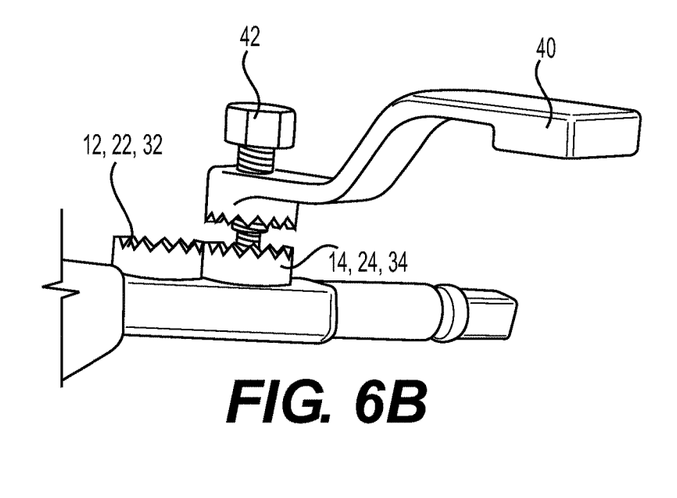
Figure 6C:
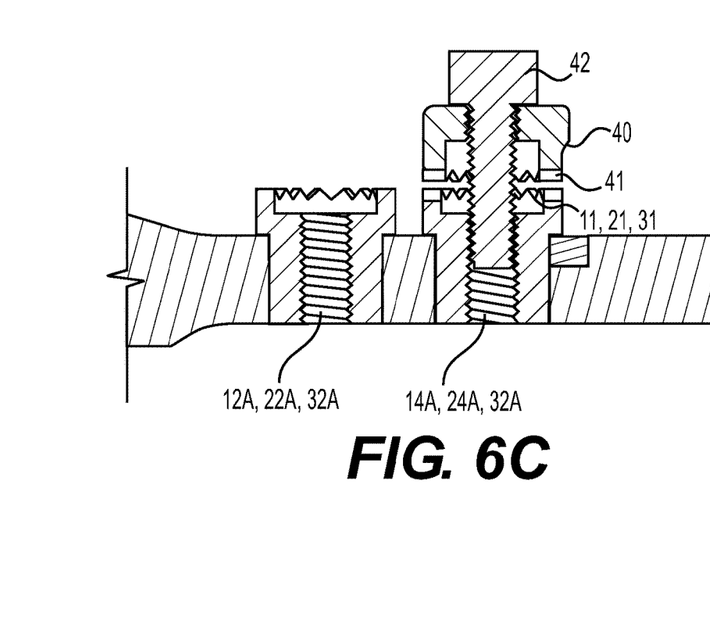
Figure 6D:
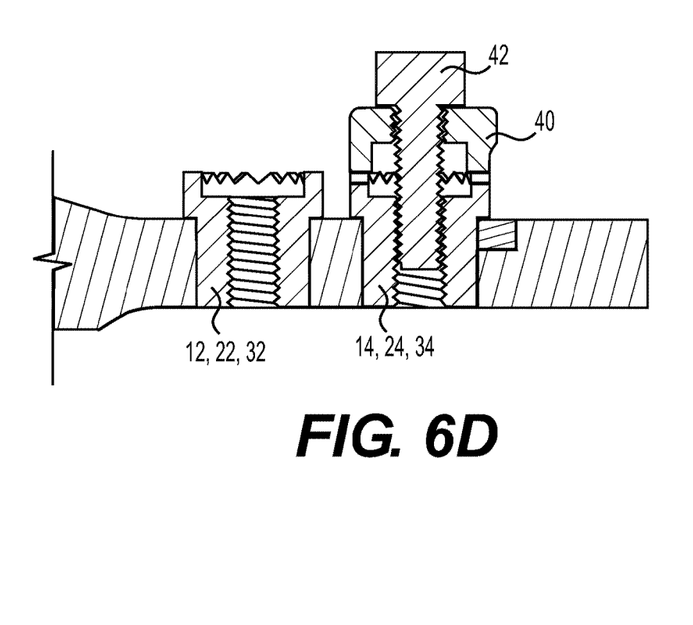
Figure 6E:
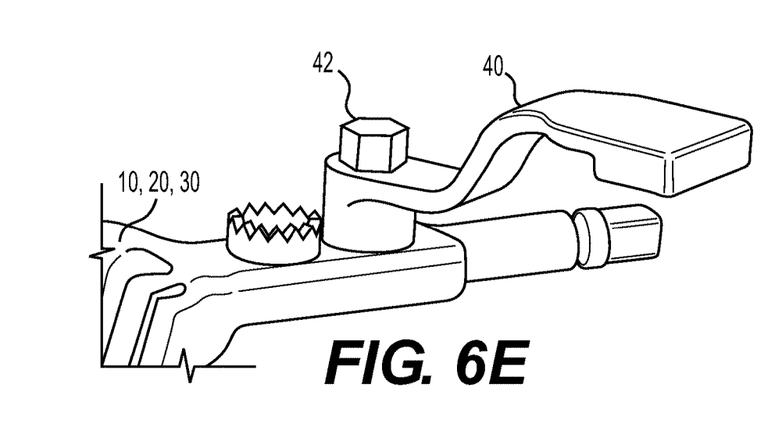
FIGS. 6E-6H shows a fully seated blade to arm connection and various blade to blade connection mechanisms.
Figure 6F:
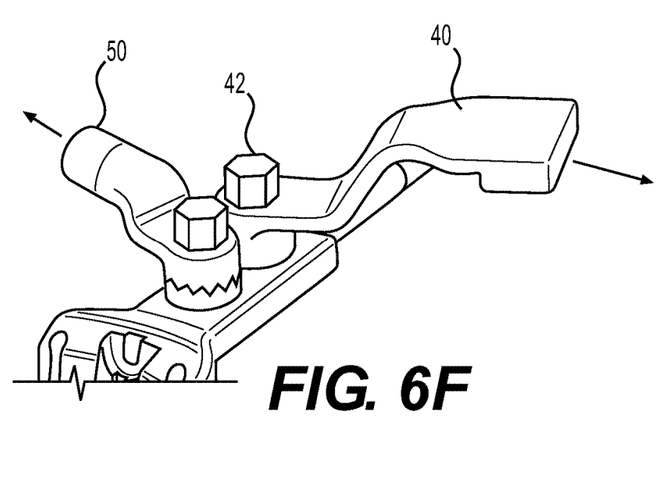
Figure 6G:
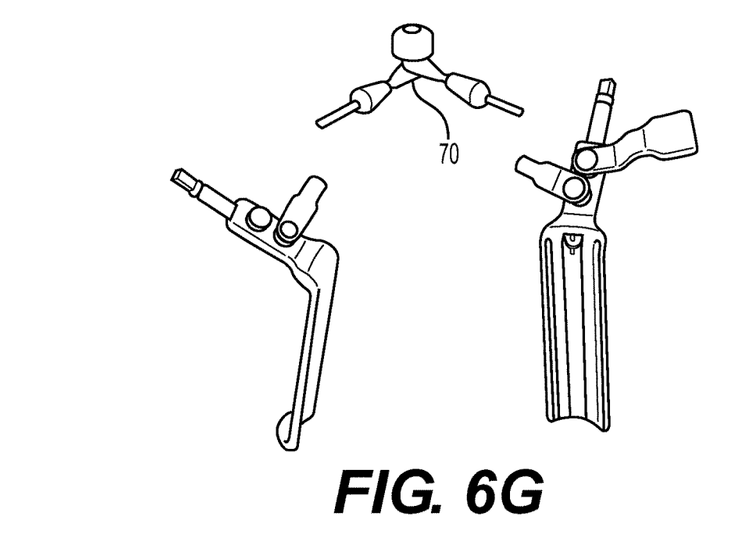
Figure 6H:
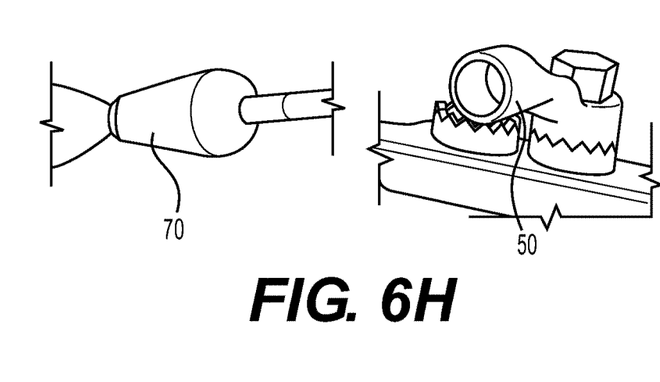

Referring to FIGS. 6A through 6H, FIG. 6A shows the two connection points 12, 14, 22, 24 and 32, 34 per blades 10, 20, 30 respectively. A threaded fastener 42 secures the arm connector 40 to each respective blade 1, 20, 30. When the fastener 42 is tightened into threads 12A, 14A, 22A, 24A, 32A, 34A, the corresponding teeth 41 of the arm connector 40 are aligned with the teeth 11, 21, 31 of each blade 10, 20, 30 thereby fixing the arm connector 40 to the respective blade as shown in FIGS. 6B through 6D. In FIGS. 6E through 6H, the use of the min flex arm 70 is shown, the mini flex arm 70 couples the blades 10, 20, 30 at the blade connectors 50.

Figure 7A:
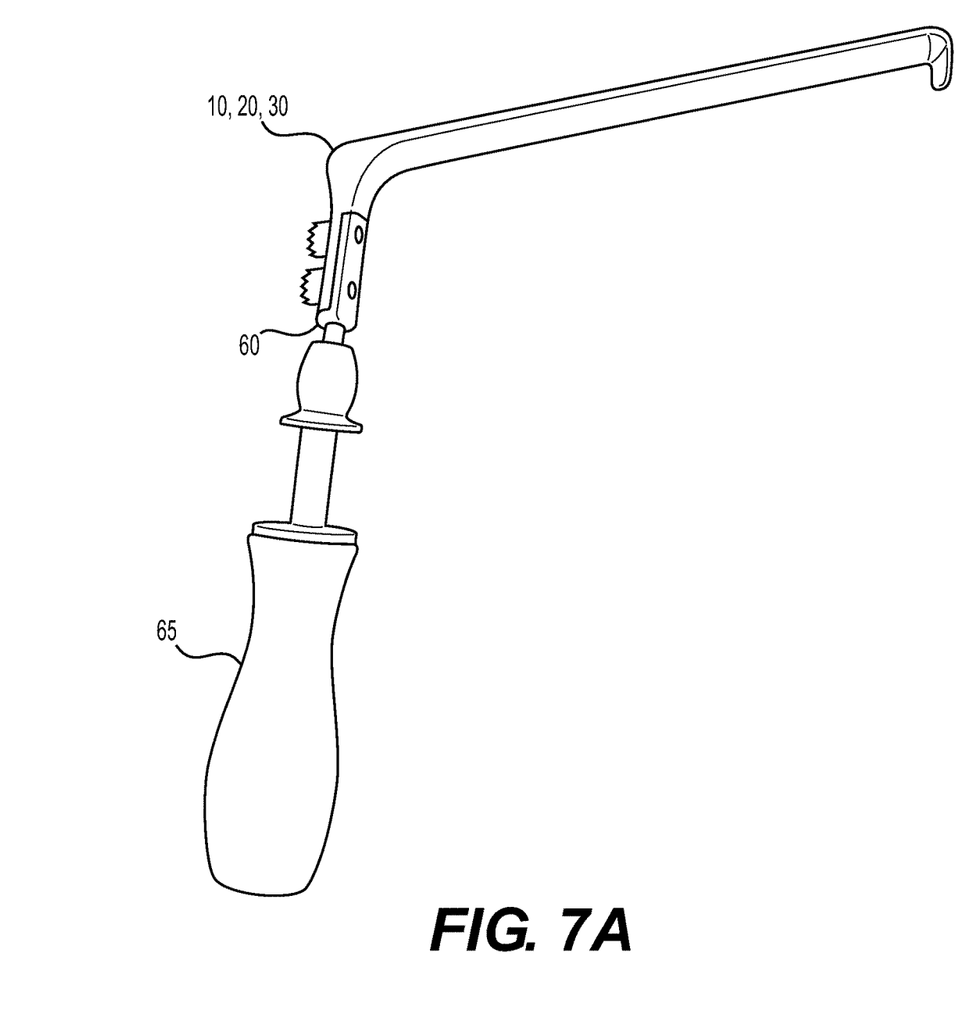
FIGS. 7A and 7B show side and top views respectively of the quick connect handle attached to a blade.
Figure 7B:
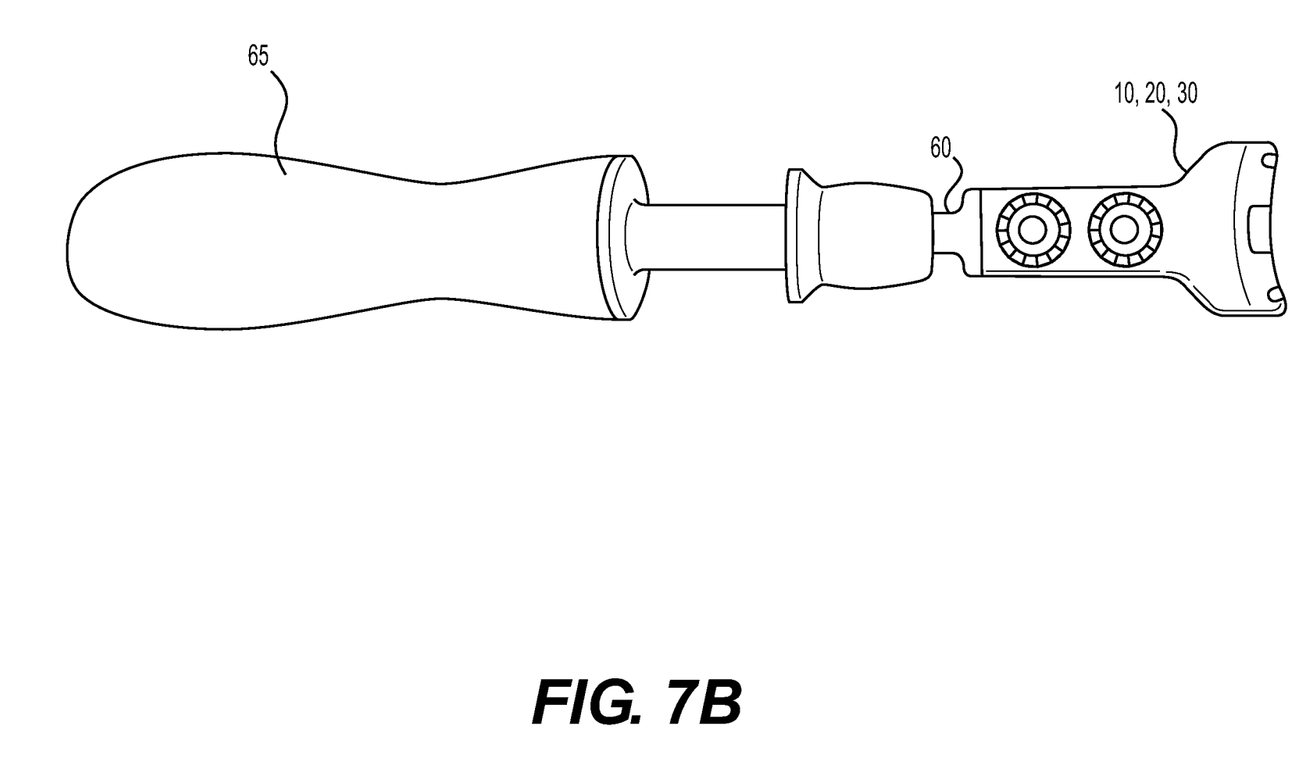

With reference to FIGS. 7 A and 7B, handle 65 is shown connected to the handle quick connect 60 which is attached to a blade 10, 20, 30.

Using a handle quick connect 60 attached to the blades, the surgeon will place #1 Blade 10 into the exposure and position as desired. A blade to arm connector 40 will then be used to connect #1 Blade 10 to a table arm. The handle from the handle quick connect 60 may be removed. The same will be done for #3 Blade 30. #2 Blade 20 will be inserted into the exposure and positioned as desired. Using a mini flex arm 70 and blade to blade connectors 50, #2 Blade 20 will be connected to either #1 Blade 10 or #3 Blade 30. The handle may be removed. A blade to blade connector 50 and mini flex arm 70 may be substituted for the blade to arm connector 40 and table arm for either #1 Blade 10 or #3 Blade 30.

Figure 8:
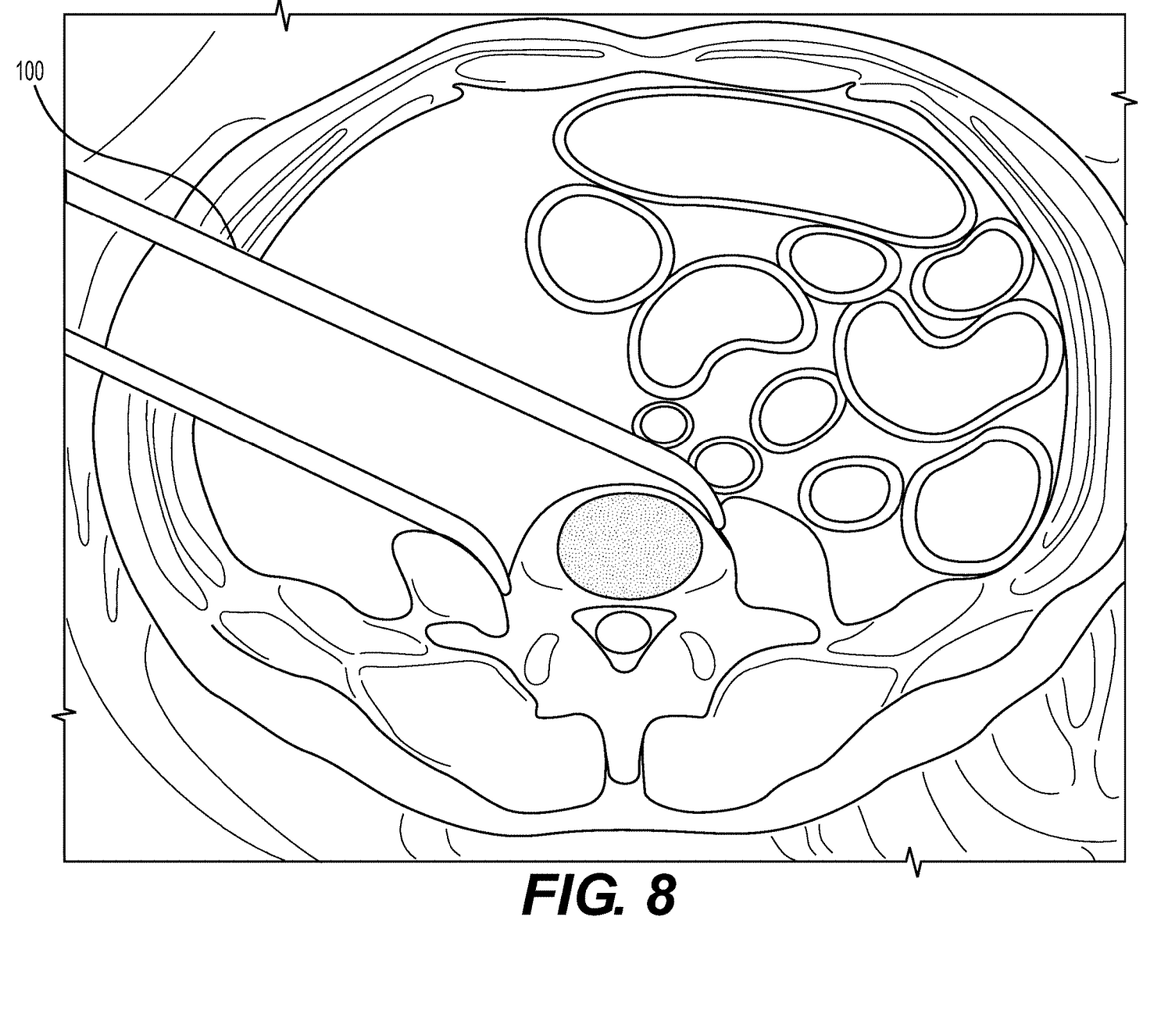
FIG. 8 shows a depiction of an OLIF implant specifically designed for an OLIF approach (approximately 25° off the coronal plane) being implanted.

Once retraction is complete, discectomy and endplate preparation will be completed. Next, an implant preferably specifically designed for the OLIF approach (approximately 25° off the coronal plane) will be implanted, as shown in FIG. 8. The OLIF implant 2 is designed to be inserted without the use of an orthogonal maneuver. When inserted using an approach 25° off the coronal plane, the lordosis of the implant will be correctly aligned with the lordosis of the spine.

Figure 9A:
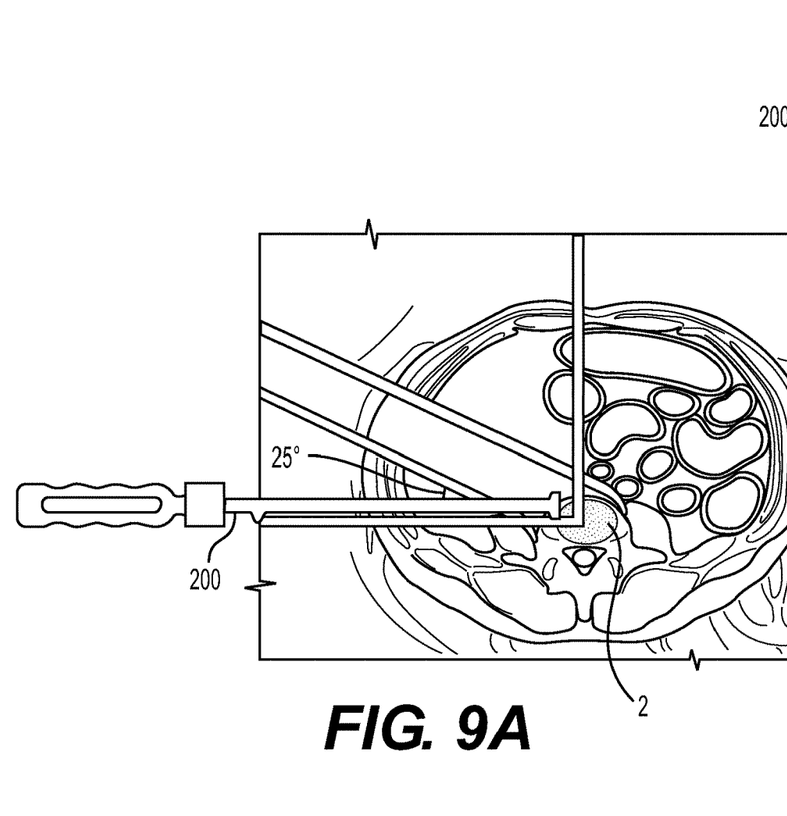
FIGS. 9A and 9B show the OLIF implant may be inserted using a straight or articulating inserter respectively. The articulating inserter allows the surgeon to adjust the angle of the inserter handle relative to the implant. This may be used to adjust the trajectory of the implant prior to inserting into the disc space or after.
Figure 9B:
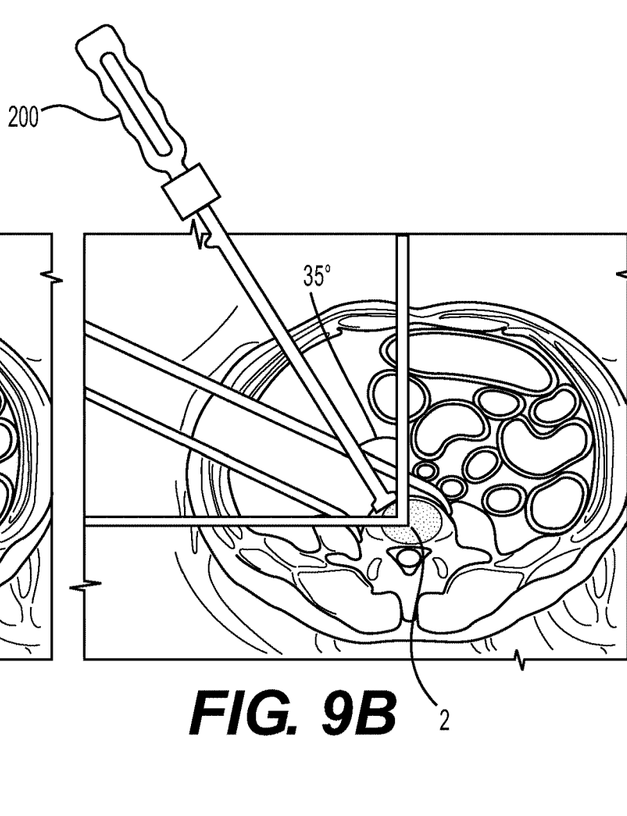

The implant may be inserted using a straight or articulating inserter 200 as shown in FIGS. 9A, 9B. The articulating inserter 200 allows the surgeon to adjust the angle of the inserter handle relative to the implant. This may be used to adjust the trajectory of the implant prior to inserting into the disc space or after.

While the retractor system 100 with inserter 200 is design specifically for an OLIF approach at L5-S1 between the bifurcation, it can also be utilized for an OLIF approach at levels higher up in the lumbar spine. Furthermore, the retractor blades could be utilized for any surgical approach, spine or otherwise, that requires soft tissue retraction.

Figure 10:
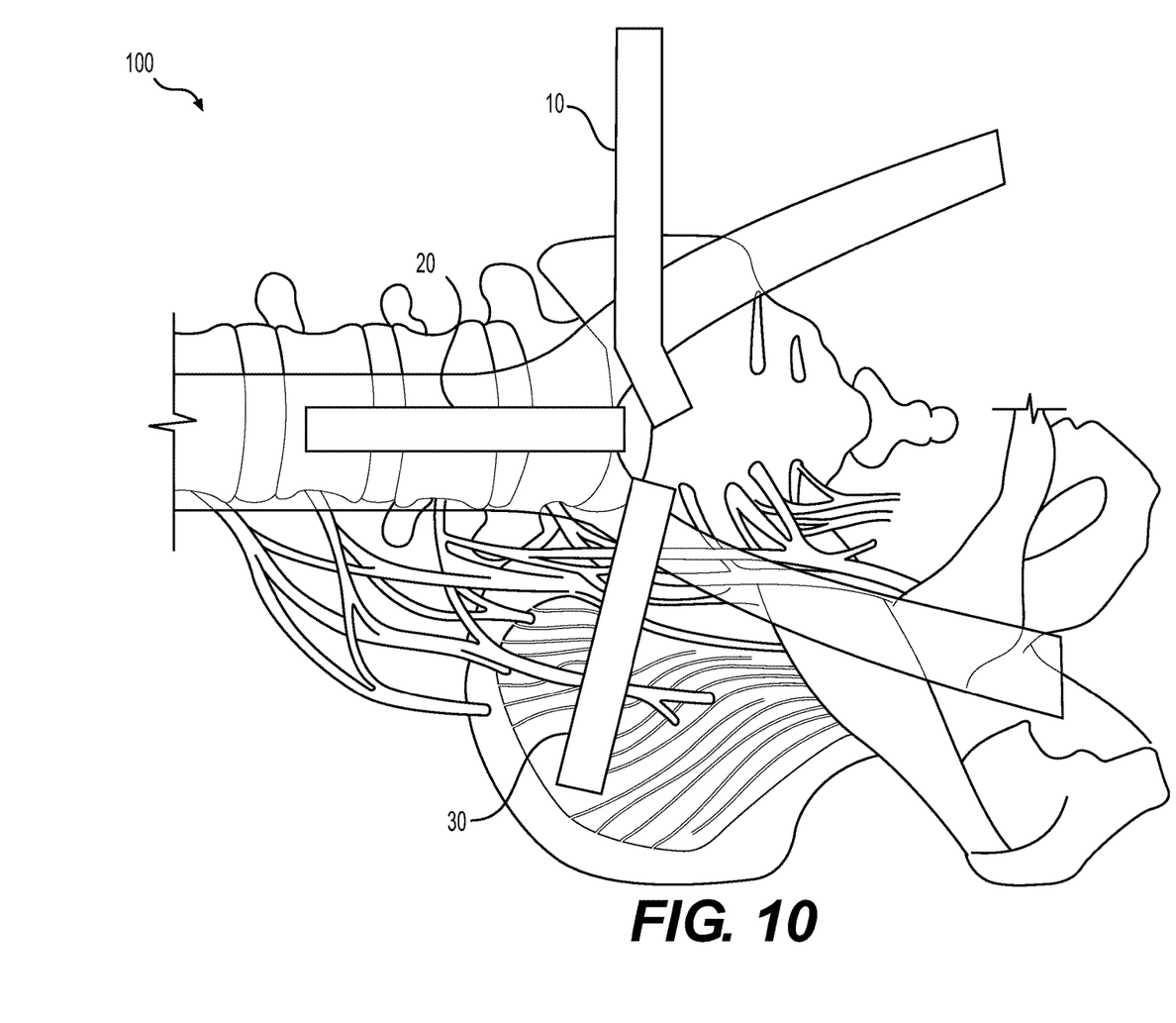
FIG. 10 shows a three blade retraction.

FIG. 10 shows an exemplary three blade retraction.

A particularly unique feature of this system 100 is the ability to build the rigid frame outside of the body after the blades have been properly positioned by hand and pinned to a vertebral body.

Additionally, the overall system 100 eliminates the orthogonal maneuver during implant insertion and gives the ability to dial in the trajectory of the implant relative to the inserter handle during an OLIF approach.

The advantage of this system is that the surgeon has the flexibility to place the blades wherever they want without being limited by the rigid frame. This ensures that the blades are placed perfectly every time based on unique anatomic structures while still providing a rigid frame.

Placing the retractor blades 10, 20, 30 by hand provides the surgeon with tactile feedback to help reduce the risk of vascular injury.

Blade to blade fixation eliminates the need for someone (typically a physician assistant) to hold one of the blades in place during the procedure. If two blade to blade connections are used, this eliminates the need for a second table arm and removes clutter from the sterile field.

The elimination of the orthogonal maneuver during implant insertion simplifies the procedure.

The ability to dial in the trajectory of the implant relative to the inserter handle during an OLIF approach allows the surgeon to correct the axial rotation of the implant relative to the disc space. This may be necessary due patient anatomy preventing an ideal approach angle.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of positioning a spinal implant into an intervertebral space comprising the steps of:
   cutting an incision through the skin toward an intervertebral space between an L5 vertebra and an S1 vertebra of a patient;
   inserting an uncoupled first retractor blade, second retractor blade, and third retractor blade into the incision;
   independently moving the first retractor blade, the second retractor blade, and the third retractor blade manually to retract tissues of the patient about the incision to pre-position the retractor blades in a retracted position;
   securing the retractor blades in the retracted position by:
      coupling the pre-positioned first retractor blade to a connector arm to connect the first retractor blade to a table arm; and
      attaching a first blade to blade connector to the second retractor blade, attaching a second blade to blade connector to the first retractor blade or the third retractor blade, and attaching a mini flex arm to the first blade to blade connector and the second blade to blade connector in order to couple the second retractor blade to the first retractor blade or the third retractor blade in the retracted position.

2. The method of claim 1 wherein one or more of the blades include threaded Steinmann pins and the method includes securing one or more of the blades to the vertebra with one or more of the threaded Steinmann pins.

3. The method of claim 1 wherein at least one of the retractor blades includes a handle attached with a handle quick connect in order to facilitate manually pre-positioning the at least one retractor blade.

4. The method of claim 3 wherein the method further comprises detaching the handle quick connect once the at least one retractor blade is pre-positioned and secured in the retracted position.

5. The method of claim 1 wherein once the retractors have been secured in the retracted position, performing steps of discectomy and end plate preparation.

6. The method of claim 5 further comprises implanting an implant between the L5 vertebra and the S1 vertebra of the patient via an opening defined by the retractor blades secured in the retracted position.

7. The method of claim 6 wherein if the implant is inserted using an inserter on an OLIF approach of approximately 25 degrees off a coronal plane of the patient, an axis in which lordosis of the implant is oriented will be in alignment with an axis in which lordosis of the spine of the patient is oriented.

8. The method of claim 6, wherein the implant is inserted without the use of an orthogonal maneuver in which the implant is inserted along the coronal plane or the sagittal plane.

9. The method of claim 8 wherein the implant is inserted using an OLIF approach approximately 25 degrees off a coronal plane of the patient.

10. The method of claim 9 wherein the implant is inserted using an articulating inserter.

11. The method of claim 10 wherein the articulating inserter allows the surgeon to adjust the angle of a handle of the inserter relative to the implant to adjust the trajectory of the implant.

\* \* \* \* \*